(12) United States Patent
Watanabe et al.

(10) Patent No.: US 9,695,186 B2
(45) Date of Patent: Jul. 4, 2017

(54) ALICYCLIC DIEPOXY COMPOUND HAVING BIS-SPIRONORBORNANE STRUCTURE, METHOD FOR PRODUCING THE SAME, AND USE THEREOF

(71) Applicant: JX NIPPON OIL & ENERGY CORPORATION, Tokyo (JP)

(72) Inventors: Daisuke Watanabe, Tokyo (JP); Takaya Matsumoto, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 15/305,476

(22) PCT Filed: Apr. 22, 2015

(86) PCT No.: PCT/JP2015/062221
§ 371 (c)(1),
(2) Date: Oct. 20, 2016

(87) PCT Pub. No.: WO2015/163362
PCT Pub. Date: Oct. 29, 2015

(65) Prior Publication Data
US 2017/0044179 A1 Feb. 16, 2017

(30) Foreign Application Priority Data

Apr. 25, 2014 (JP) ................. 2014-092111

(51) Int. Cl.
| C07D 493/10 | (2006.01) |
| C07D 303/32 | (2006.01) |
| C07D 301/12 | (2006.01) |
| C08G 59/24 | (2006.01) |

(52) U.S. Cl.
CPC ......... *C07D 493/10* (2013.01); *C07D 301/12* (2013.01); *C07D 303/32* (2013.01); *C08G 59/24* (2013.01)

(58) Field of Classification Search
CPC ............................ C07D 493/10; C07D 303/32
USPC ....................................................... 549/330
See application file for complete search history.

(56) References Cited

U.S. PATENT DOCUMENTS

| 2010/0249341 A1 | 9/2010 | Sato et al. |
| 2012/0310013 A1 | 12/2012 | Komatsu et al. |
| 2013/0079490 A1 | 3/2013 | Matsumoto et al. |
| 2015/0141675 A1 | 5/2015 | Ichihara et al. |

FOREIGN PATENT DOCUMENTS

| JP | S62-33183 A | 2/1987 |
| JP | 2000-196151 A | 7/2000 |
| JP | 2003-277473 A | 10/2003 |
| JP | 2004-099445 A | 4/2004 |
| JP | 2004-175769 A | 6/2004 |
| JP | 2006-273748 A | 10/2006 |
| JP | 2008-031424 A | 2/2008 |
| JP | 2011-162479 A | 8/2011 |
| JP | 2013-053097 A | 3/2013 |
| JP | 2013-241374 A | 12/2013 |
| WO | 2011/099518 A1 | 8/2011 |

OTHER PUBLICATIONS

Bascoul, Jacques et al., "Dimensional analogs of steroid hormones," Comptes Rendus Des Seances De L'Academie Des Sciences, Serie C: Sciences Chimiques, (1967), vol. 264, No. 7, pp. 629-632.
Jul. 28, 2015 Search Report issued in International Patent Application No. PCT/JP2015/062221.

*Primary Examiner* — Niloofar Rahmani
(74) *Attorney, Agent, or Firm* — Oliff PLC

(57) ABSTRACT

An alicyclic diepoxy compound represented by the following general formula (1):

[Chem. 1]

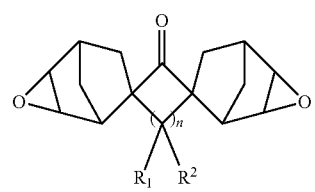

(1)

(in the general formula (1), $R^1$ and $R^2$ each independently represent one selected from the group consisting of a hydrogen atom, alkyl groups having 1 to 10 carbon atoms, and a fluorine atom, and n represents an integer of 2 to 5).

10 Claims, 4 Drawing Sheets

ALICYCLIC DIEPOXY COMPOUND HAVING BIS-SPIRONORBORNANE STRUCTURE, METHOD FOR PRODUCING THE SAME, AND USE THEREOF

TECHNICAL FIELD

The present invention relates, in particular, to a multifunctional compound usable for a polymer material obtained through a condensation reaction or a curing reaction, wherein the multifunctional compound is an alicyclic diepoxy compound which gives a polymer material excellent in transparency and heat resistance, as well as a method for producing the alicyclic diepoxy compound and a production intermediate of the alicyclic diepoxy compound. In addition, the alicyclic diepoxy compound relating to the present invention can be chemically modified, and hence can also be used as a reaction intermediate of various compounds.

BACKGROUND ART

Recent high-performance polymer materials used in the field of optics have been required to have both high transmittance of and light resistance (weatherability) against blue light to ultraviolet light (with wavelengths of 500 nm to 380 nm) mainly from the viewpoint of their mode of use and heat resistance in a soldering step mainly from the viewpoint of their manufacturing process. Hence, attempts have been made to replace an aromatic compound in a polymer material with an alicyclic compound (see, for example, PTL 1 to 5). These attempts have achieved some success, but further improvement has been awaited.

Note that, in the field of polyimide-based materials, the applicant of the present application has disclosed a tetracarboxylic acid having a bis-spironorbornane structure and derivatives thereof as compounds having an alicyclic structure usable for producing polyimide-based materials excellent in light transmittance and heat resistance; however, no diepoxy compound having a bis-spironorbornane structure has been disclosed (PTL 6 and 7).

CITATION LIST

Patent Literature

[PTL 1] Japanese Unexamined Patent Application Publication No. 2000-196151
[PTL 2] Japanese Unexamined Patent Application Publication No. 2003-277473
[PTL 3] Japanese Unexamined Patent Application Publication No. 2006-273748
[PTL 4] Japanese Unexamined Patent Application Publication No. 2008-31424
[PTL 5] Japanese Unexamined Patent Application Publication No. 2013-53097
[PTL 6] International Publication No. WO2011-099518
[PTL 7] Japanese Unexamined Patent Application Publication No. 2011-162479

SUMMARY OF INVENTION

Technical Problem

An object of the present invention is mainly to provide an alicyclic diepoxy compound effectively usable for providing a polymer material excellent in light transmittance and heat resistance, a method for producing the alicyclic diepoxy compound, and a production intermediate of the alicyclic diepoxy compound.

Solution to Problem

The present inventors have conducted intensive and continuous studies to achieve the above-described object, and consequently have found that an alicyclic diepoxy compound obtained by introducing symmetry to the alicyclic structure serving as the basic skeleton, while excluding a carbon-carbon single bond which may undergo free rotation is effectively usable for producing a polymer material extremely excellent in both light transmittance and heat resistance. This finding has led to the completion of the present invention.

Specifically, a first aspect of the present invention relates to an alicyclic diepoxy compound represented by the following general formula (1):

[Chem. 1]

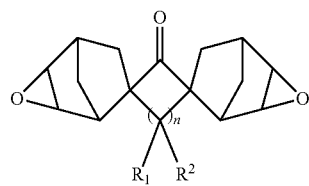

(1)

(in the formula (1), $R^1$ and $R^2$ each independently represent one selected from the group consisting of a hydrogen atom, alkyl groups having 1 to 10 carbon atoms, and a fluorine atom, and n represents an integer of 2 to 5).

A second aspect of the present invention relates to the alicyclic diepoxy compound according to the first aspect of the present invention, wherein n in the general formula (1) is 2 or 3.

A third aspect of the present invention relates to the alicyclic diepoxy compound according to the first aspect of the present invention, wherein n in the general formula (1) is 2.

A fourth aspect of the present invention relates to a method for producing an alicyclic diepoxy compound having a bis-spironorbornane structure represented by the following general formula (1), the method comprising: epoxidizing one carbon-carbon unsaturated bond in a compound having a bis-spironorbornene structure represented by the following general formula (2) to obtain a monoepoxy compound represented by the following general formula (3); and epoxidizing another carbon-carbon unsaturated bond in the obtained compound to obtain the diepoxy compound having the bis-spironorbornane structure represented by the following general formula (1):

[Chem. 2]

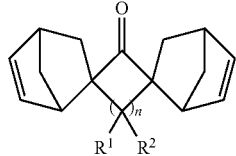

(2)

(in the general formula (2), $R^1$ and $R^2$ each independently represent one selected from the group consisting of a hydrogen atom, alkyl groups having 1 to 10 carbon atoms, and a fluorine atom, and n represents an integer of 2 to 5);

[Chem. 3]

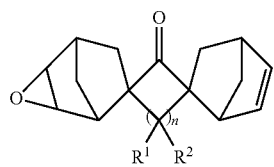

(3)

(in the general formula (3), $R^1$ and $R^2$ each independently represent one selected from the group consisting of a hydrogen atom, alkyl groups having 1 to 10 carbon atoms, and a fluorine atom, and n represents an integer of 2 to 5); and

[Chem. 4]

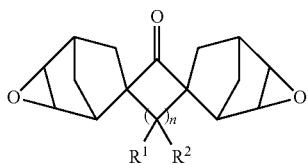

(1)

(in the general formula (1), $R^1$ and $R^2$ each independently represent one selected from the group consisting of a hydrogen atom, alkyl groups having 1 to 10 carbon atoms, and a fluorine atom, and n represents an integer of 2 to 5).

A fifth aspect of the present invention relates to the method for producing an alicyclic diepoxy compound according to the fourth aspect of the present invention, wherein n in the general formula (1) is 2 or 3.

A sixth aspect of the present invention relates to the method for producing an alicyclic diepoxy compound according to the fourth aspect of the present invention, wherein n in the general formula (1) is 2.

A seventh aspect of the present invention relates to an alicyclic monoepoxy compound having an epoxy group and represented by the following general formula (3):

[Chem. 5]

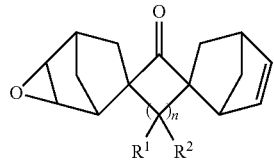

(3)

(in the general formula (3), $R^1$ and $R^2$ each independently represent one selected from the group consisting of a hydrogen atom, alkyl groups having 1 to 10 carbon atoms, and a fluorine atom, and n represents an integer of 2 to 5).

An eighth aspect of the present invention relates to the alicyclic monoepoxy compound having the bis-spironorbornane structure according to the seventh aspect of the present invention, wherein n in the general formula (3) is 2 or 3.

A ninth aspect of the present invention relates to the alicyclic monoepoxy compound having the bis-spironorbornane structure according to the seventh aspect of the present invention, wherein n in the general formula (3) is 2.

A tenth aspect of the present invention relates to the method for producing an alicyclic diepoxy compound according to the fourth to sixth aspects of the present invention, wherein an epoxidation reaction is conducted in the presence of a hydrogen peroxide solution, a heteropoly acid catalyst, and a surfactant.

An eleventh aspect of the present invention relates to use of the alicyclic diepoxy compound according to any one of the first to third aspects of the present invention as a monomer for a polymer material. In other words, the eleventh aspect of the present invention relates to a monomer for producing a polymer material, comprising the alicyclic diepoxy compound according to any one of the first to third aspects of the present invention.

Advantageous Effects of Invention

The present invention makes it possible to provide an alicyclic diepoxy compound effectively usable for providing a polymer material excellent in light transmittance and heat resistance, as well as a method for producing the alicyclic diepoxy compound and a production intermediate of the alicyclic diepoxy compound.

Note that the novel alicyclic diepoxy compound represented by the above-described general formula (1) according to the present invention has symmetry because the alicyclic structure serving as the basic skeleton has a bis-spironorbornane structure, but this alicyclic diepoxy compound has no carbon-carbon single bond which may undergo free rotation. Hence, the novel alicyclic diepoxy compound is useful as a monomer for producing a polymer material having a high transparency and a high heat resistance. In addition, the alicyclic diepoxy compound has a more suitable size as a monomer molecule and higher solubilities in organic solvents and hence easier to handle in a manufacturing process of the polymer material, compared to other multifunctional compounds used for heat-resistant polymer materials. In addition, these compounds including the intermediates thereof are applicable also in the fields of reaction intermediates of various useful compounds such as pharmaceuticals and agricultural chemicals.

DESCRIPTION OF EMBODIMENTS

Figure 1:
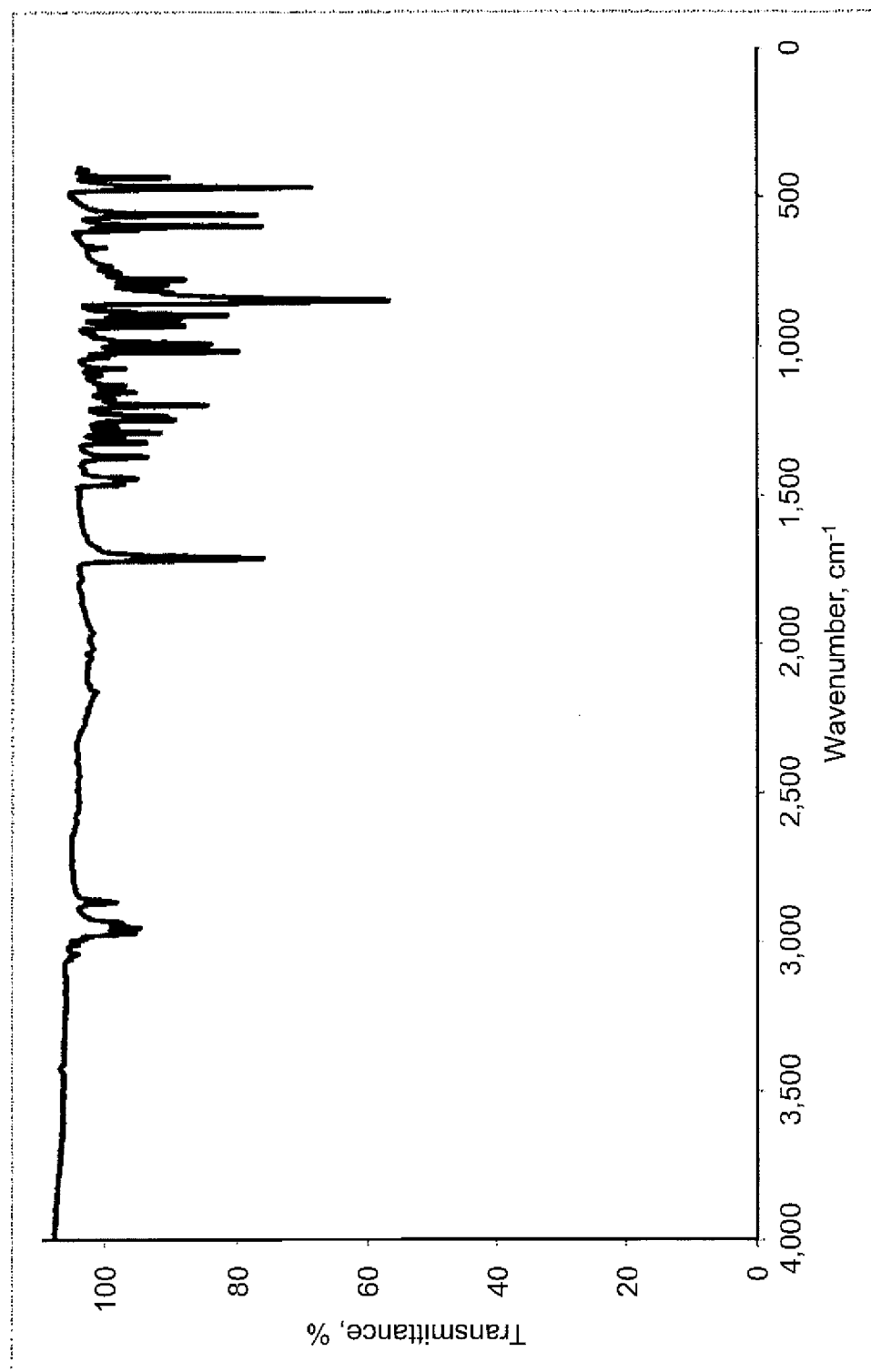
FIG. 1 is a chart showing an IR spectrum of an alicyclic diepoxy compound represented by chemical formula (6) and obtained in Example 1.

Structure of Alicyclic Diepoxy Compound of the Present Invention

An alicyclic diepoxy compound according to the present invention is represented by the following general formula (1):

[Chem. 6]

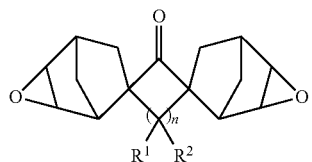

(in the general formula (1), R¹ and R² each independently represent one selected from the group consisting of a hydrogen atom, alkyl groups having 1 to 10 carbon atoms, and a fluorine atom, and n represents an integer of 2 to 5).

The alicyclic diepoxy compound according to the present invention has, as a base structure, a bis-spironorbornane structure which has norbornane rings at symmetric positions of a cycloalkanone, which is highly symmetric, and which has no freely rotatable carbon-carbon bond. As of now, no example of production of an alicyclic diepoxy compound having this base structure has been known.

Note that the general formula (1) collectively represents multiple isomers which have the conformational relationships between the cycloalkanone ring and each norbornane ring and between each norbornane ring and the epoxy group.

In the field of heat-resistant polymer materials, it is empirically known that a compound (monomer) having a structure which lowers the rigidity or symmetry of the molecular chain of a polymer material is highly likely to lower the heat resistance of the polymer material. In addition, it is empirically known that a compound (monomer) having a freely rotatable carbon-carbon bond has the same tendency.

It is also known that when a compound (constituent monomer) to constitute a polymer material has a bulkier structure than another compound (constituent monomer) to constitute the polymer material or has a poor solubility in the solvent used in the reaction system, the compound having the bulkier structure or the poor solubility may be insufficiently incorporated into the polymer material.

The alicyclic diepoxy compound according to the present invention solves these problems by arranging, into a symmetric structure, alicyclic structures each having a similar number of carbon atoms to those of aromatic rings in an aromatic compound (monomer) included in a heat-resistant polymer material, and linking these alicyclic structures to each other by spiro bonding which does not allow the free rotation. In addition, since a carbonyl group having an oxygen atom which has unshared electron pairs is contained, the formation of intramolecular and intermolecular hydrogen bonds of the polymer chains improves the heat resistance.

As described above, the alicyclic diepoxy compound of the present invention is useful as a monomer for producing a polymer material, and is particularly useful as a monomer for producing a polymer material having a high transparency and a high heat resistance.

Note that the alkyl group which can be selected as each of R¹ and R² in the general formula (1) is an alkyl group having 1 to 10 carbon atoms. If the number of carbon atoms exceeds 10, the heat resistance of a cured product obtained by using such an alicyclic diepoxy compound as a monomer for an epoxy resin is lowered. In addition, the number of carbon atoms of the alkyl group which can be selected as each of R¹ and R² is preferably 1 to 6, more preferably 1 to 5, further preferably 1 to 4, and particularly preferably 1 to 3 from the viewpoint that a higher heat resistance can be obtained when an epoxy cured product is produced. In addition, the alkyl group which can be selected as each of R¹ and R² may be linear or branched.

R¹ and R² in the general formula (1) are each independently more preferably a hydrogen atom, a methyl group, an ethyl group, a n-propyl group, or an isopropyl group, and particularly preferably a hydrogen atom or a methyl group, from the viewpoint that a higher heat resistance can be obtained when an epoxy cured product is produced. In addition, R¹ and R² in the formula may be the same as or different from each other, and are preferably the same from the viewpoints of ease of purification and the like.

In addition, n in the general formula (1) represents an integer of 2 to 5. If the value of n exceeds the upper limit, it is difficult to purify the bis-spironorbornanes represented by the general formula (1). Meanwhile, if the value of n is smaller than the lower limit, it is difficult to synthesize the bis-spironorbornanes represented by the general formula (1). Moreover, the value of n is preferably 2 or 3, and particularly preferably 2, from the viewpoint of the stability of the structure of the bis-spironorbornane compound represented by the general formula (1).

(Method for Producing Alicyclic Diepoxy Compound of the Present Invention)

The alicyclic diepoxy compound according to the present invention is preferably produced by using a bis-spironorbornene compound having the corresponding structure to that of the alicyclic diepoxy compound, i.e., a bis-spironorbornene compound represented by the following general formula (2) as a raw material through chemical modifications to the unsaturated bonds in the compound. A method for producing the compound represented by the following general formula (2) is disclosed in PTL 7 (paragraphs [0119] to [0132]) filed by the applicant of the present application:

[Chem. 7]

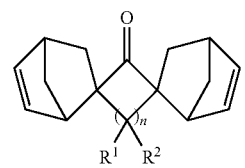

(in the general formula (2), R¹ and R² each independently represent one selected from the group consisting of a hydrogen atom, alkyl groups having 1 to 10 carbon atoms, and a fluorine atom, and n represents an integer of 2 to 5).

The compound having the bis-spironorbornene structure produced by the production method disclosed in PTL 7 (see also Examples described later) can be used in the form of the reaction mixture liquid, as it is, without isolation, or may be used after isolation and purification for the subsequent reaction.

Note that compounds having a bis-spironorbornene structure which has cycloheptanone or cyclooctanone as the skeleton can also be synthesized in the same manner as described above.

Hereinafter, a method for producing the alicyclic diepoxy compound according to the present invention from the above-described bis-spironorbornene compound is described.

To produce the alicyclic diepoxy compound according to the present invention from the bis-spironorbornene compound, it is preferable to epoxidize the carbon-carbon double bonds, and this can be performed by any of the known methods. Of these methods, a combination of a heteropoly acid catalyst with a peroxy acid is preferable, because it is simple. Note that the method capable of epoxidizing the carbon-carbon double bonds of the bis-spironorbornene compound is not limited to the method using the combination of a heteropoly acid catalyst with a peroxy acid (a heteropoly acid catalyst does not necessarily have to be used), but various methods can be employed, as appropriate. For example, it is also possible to employ a method in which the carbon-carbon double bonds are epoxidized by utilizing an oxidation reaction using meta-chloroperoxybenzoic acid.

Examples of the peroxy acid include inorganic acids such as a hydrogen peroxide solution, organic peroxy acids such as peroxyformic acid, peroxyacetic acid, peroxypropionic acid, peroxymaleic acid, peroxybenzoic acid, m-chloroperoxybenzoic acid, and peroxyphthalic acid, and acid anhydrides thereof. Of these peroxy acids, the hydrogen peroxide solution is preferably used.

As the hydrogen peroxide solution, commercially available one can be used as it is. The molar amount of hydrogen peroxide used is preferably in a range from 2.0 to 5.0 times and more preferably in a range from 2.2 to 3.0 times that of the carbon-carbon unsaturated bonds in the bis-spironorbornene compound serving as the raw material compound. If the molar amount of hydrogen peroxide used is smaller than 2.0 times, the reaction does not proceed sufficiently. Meanwhile, if the molar amount of hydrogen peroxide used exceeds 5.0 times, side reactions such as oxidative decomposition of the epoxy rings of the produced alicyclic diepoxy compound tend to proceed, resulting in decrease in yield.

A reaction temperature is preferably in a range from 30 to 80° C. If the reaction temperature is lower than 30° C., the reaction rate is extremely low, and the reaction efficiency is poor. If the reaction temperature exceeds 80° C., decomposition of the raw material and the product may occur.

The mole ratio of the heteropoly acid to the hydrogen peroxide solution in terms of hydrogen peroxide is preferably in a range from 1:100 to 1:400. The mole ratio is more preferably in a range from 1:150 to 1:250 considering the reaction efficiency.

Hereinafter, a method for producing an alicyclic diepoxy compound having a bis-spironorbornane structure represented by the above-described general formula (1) of the present invention is described in further detail (hereinafter, this method is sometimes simply referred to as "method for producing an alicyclic diepoxy compound").

The method for producing an alicyclic diepoxy compound of the present invention comprises: epoxidizing one carbon-carbon unsaturated bond in the compound having the norbornene structure represented by the above-described general formula (2) to obtain the alicyclic monoepoxy compound represented by the above-described general formula (3); and then epoxidizing another carbon-carbon unsaturated bond in the obtained compound to obtain the alicyclic diepoxy compound represented by the above-described general formula (1).

Note that, regarding the compound having the norbornene structure represented by the above-described general formula (2) used in the method for producing an alicyclic diepoxy compound, $R^1$, $R^2$, and n in the above-described general formula (2) have the same meanings as those of $R^1$, $R^2$, and n in the above-described general formula (1), and preferred ones thereof are also the same. In addition, the alicyclic diepoxy compound having the bis-spironorbornane structure represented by the above-described general formula (1) and obtained by the method for producing an alicyclic diepoxy compound is the same as the above-described alicyclic diepoxy compound of the present invention (preferred examples of $R^1$, $R^2$, and n in formula (1) are also the same).

In addition, in the method for producing an alicyclic diepoxy compound, the alicyclic monoepoxy compound represented by the above-described general formula (3) is first obtained by epoxidizing one carbon-carbon double bond in the compound having the norbornene structure represented by the above-described general formula (2). A method for epoxidizing one carbon-carbon double bond in the compound having the norbornene structure represented by the general formula (2) is not particularly limited, and a known method capable of epoxidizing a carbon-carbon double bond can be used, as appropriate. For example, the method for epoxidation using a combination of a heteropoly acid catalyst with a peroxy acid as described above may be employed. Note that, as the method for using the heteropoly acid catalyst and the peroxy acid and the reaction conditions, the above-described conditions can be employed, as appropriate. In addition, when the reaction temperature is kept in the epoxidation step, the reaction proceeds even after the alicyclic monoepoxy compound is formed by the epoxidation, so that the alicyclic monoepoxy compound is further epoxidized to the alicyclic diepoxy compound. Here, by stopping the reaction in the middle (for example, by not performing the heating step for a sufficient period, but stopping the heating in the middle, or by other means), it is also possible to make the alicyclic monoepoxy compound coexistent in the product. This makes it possible to obtain the alicyclic monoepoxy compound (reaction intermediate).

In addition, for the epoxidation in the method for producing an alicyclic diepoxy compound, the epoxidation reaction is conducted more preferably in the presence of a hydrogen peroxide solution, a heteropoly acid catalyst, and a surfactant.

Examples of the surfactant include chlorides such as tetrahexylammonium chloride, tetrabutylammonium chloride, tetrapropylammonium chloride, tetraethylammonium chloride, tetramethylammonium chloride, trioctylmethylammonium chloride, trioctylethylammonium chloride, dilauryldimethylammonium chloride, lauryltrimethylammonium chloride, stearyltrimethylammonium chloride, lauryldimethylbenzylammonium chloride, distearyldimethylammonium chloride, tricaprylmethylammonium chloride, didecyldimethylammonium chloride, benzyltrimethylammonium chloride, benzyltriethylammonium chloride, dicetyldimethylammonium chloride, cetyltrimethylammonium chloride, tetrabutylphosphonium chloride, tetraphenylphosphonium chloride, butylpyridinium chloride, dodecylpyridinium chloride, and cetylpyridinium chloride; bromides such as tetrahexylammonium bromide, tetrabutylammonium bromide, tetrapropylammonium bromide, tetraethylammonium bromide, tetramethylammonium bromide, trioctylmethylammonium bromide, trioctylethylammonium bromide, dilauryldimethylammonium bromide, lauryltrimethylammonium bromide, stearyltrimethylammonium bromide, lauryldimethylbenzylammonium bromide, distearyldimethylammonium bromide, tricaprylmethylammonium bromide, didecyldimethylammonium bromide, benzyltrimethylammonium bromide, benzyltriethylammonium bromide, dicetyldimethylammonium bromide, cetyltrimethylammonium bromide, tetrabutylphosphonium bromide, tetraphenylphosphonium bromide, and cetylpyridinium bromide; iodides such as tetrahexylammonium iodide, tetrabutylammonium iodide, tetrapropylammonium iodide, tetraethylammonium iodide, tetramethylammonium iodide, trioctylmethylammonium iodide, trioctylethylammonium iodide, dilauryldimethylammonium iodide, lauryltrimethylammonium iodide, stearyltrimethylammonium iodide, lauryldimethylbenzylammonium iodide, distearyldimethylammonium iodide, tricaprylmethylammonium iodide, didecyldimethylammonium iodide, benzyltrimethylammonium iodide, benzyltriethylammonium iodide, dicetyldimethylammonium iodide, tetrabutylphosphonium iodide, and tetraphenylphosphonium iodide; hydrogenphosphates such as trioctylmethylammonium hydrogenphosphate, trioctylethylammonium hydrogenphosphate, dilauryldimethylammonium hydrogenphosphate, lauryltrimethylammonium hydrogenphosphate, stearyltrimethylammonium hydrogenphosphate, lauryldimethylbenzylammonium hydrogenphosphate, stearyldimethylammonium hydrogenphosphate, tricaprylmethylammonium hydrogenphosphate, didecyldimethylammonium hydrogenphosphate, tetrabutylammonium hydrogenphosphate, benzyltrimethylammonium hydrogenphosphate, benzyltriethylammonium hydrogenphosphate, tetrabutylphosphonium hydrogenphosphate, and tetraphenylphosphonium hydrogenphosphate; hydrogensulfates such as tetrahexylammonium hydrogensulfate, tetrabutylammonium hydrogensulfate, tetrapropylammonium hydrogensulfate, tetraethylammonium hydrogensulfate, tetramethylammonium hydrogensulfate, trioctylmethylammonium hydrogensulfate, trioctylethylammonium hydrogensulfate, dilauryldimethylammonium hydrogensulfate, lauryltrimethylammonium hydrogensulfate, stearyltrimethylammonium hydrogensulfate, lauryldimethylbenzylammonium hydrogensulfate, distearyldimethylammonium hydrogensulfate, tricaprylmethylammonium hydrogensulfate, didecyldimethylammonium hydrogensulfate, benzyltrimethylammonium hydrogensulfate, benzyltriethylammonium hydrogensulfate, cetyldimethylammonium hydrogensulfate, cetyltrimethylammonium hydrogensulfate, tetrabutylphosphonium hydrogensulfate, and tetraphenylphosphonium hydrogensulfate; hydroxides such as tetrahexylammonium hydroxide, tetrabutylammonium hydroxide, tetrapropylammonium hydroxide, tetraethylammonium hydroxide, tetramethylammonium hydroxide, trioctylmethylammonium hydroxide, trioctylethylammonium hydroxide, dilauryldimethylammonium hydroxide, lauryltrimethylammonium hydroxide, stearyltrimethylammonium hydroxide, lauryldimethylbenzylammonium hydroxide, distearyldimethylammonium hydroxide, tricaprylmethylammonium hydroxide, didecyldimethylammonium hydroxide, benzyltrimethylammonium hydroxide, benzyltriethylammonium hydroxide, dicetyldimethylammonium hydroxide, and cetyltrimethylammonium cation hydroxide; and the like. Of these surfactants, cetylpyridinium chloride and cetylpyridinium bromide are preferable, and cetylpyridinium chloride is more preferable from the viewpoint of the reactivity.

Examples of the heteropoly acid catalyst include $H_3PW_{12}O_{40}$, $H_4SiW_{12}O_{40}$, $H_3PMo_{12}O_{40}$, $Na_3PMo_{12}O_{40}$, $H_3PW_{12-x}Mo_xO_{40}$, and $H_{15-x}PV_{12-x}Mo_xO_{40}$. Of these heteropoly acids, $H_3PW_{12}O_{40}$ and $H_3PMo_{12}O_{40}$ are preferable, and $H_3PW_{12}O_{40}$ is more preferable, from the viewpoint of the reactivity.

Note that, in the epoxidation reaction, as described above, the alicyclic monoepoxy compound represented by the above-described general formula (3) is formed as an intermediate, and then, by allowing the epoxidation reaction to further proceed, the alicyclic diepoxy compound having the bis-spironorbornane structure represented by the above-described general formula (1) is formed. For example, in a case where the compound having the norbornene structure represented by the above-described general formula (2), the surfactant, the hydrogen peroxide solution, and the heteropoly acid catalyst are introduced into a solvent, and the epoxidation reaction is caused to proceed by heating in the presence of the surfactant, the hydrogen peroxide solution, and the heteropoly acid catalyst, the alicyclic monoepoxy compound represented by the above-described general formula (3) is formed as an intermediate at a stage where the epoxidation has not been completed yet (when the reaction is stopped in the middle, it is also possible to take the intermediate out of the reaction system), and then the reaction is allowed to proceed by further continuing the heating. Thus, the alicyclic diepoxy compound having the bis-spironorbornane structure represented by the above-described general formula (1) can be formed. Note that, in the present invention, it is preferable to form the alicyclic diepoxy compound having the bis-spironorbornane structure represented by the above-described general formula (1) by a series of steps in which the compound having the norbornene structure represented by the above-described general formula (2), the surfactant, the hydrogen peroxide solution, and the heteropoly acid catalyst are introduced into a solvent, and the heating is continued in the presence of the surfactant, the hydrogen peroxide solution, and the heteropoly acid catalyst to cause the epoxidation to proceed sufficiently, from the viewpoint of forming the alicyclic diepoxy compound having the bis-spironorbornane structure represented by the above-described general formula (1) more efficiently.

In the epoxidation reaction, it is preferable to use a solvent from the viewpoint of controlling the reaction. The solvent is not particularly limited, and a known solvent usable for epoxidation of a carbon-carbon double bond can be used, as appropriate. For example, it is possible to use, as appropriate, any of halogen-containing solvents such as chloroform, dichloroethane, and dichloromethane; primary, secondary, or tertiary monovalent alcohols having 3 to 6 carbon atoms such as n- or iso-propanol and tertiary butanol; polyols such as propylene glycol, glycerin, diethylene glycol, and triethylene glycol; ketones such as methyl ethyl ketone, methyl isobutyl ketone, and acetylacetone; esters such as methyl acetate, ethyl acetate, propyl acetate, isopropyl acetate, n-butyl acetate, iso-butyl acetate, sec-butyl acetate, tert-butyl acetate, and methyl benzoate; and acetonitrile.

The amount of the surfactant used is not particularly limited, and the surfactant is preferably used at a ratio of 0.01 to 0.10 moles (more preferably 0.02 to 0.05 moles) per mole of the compound having the norbornene structure represented by the above-described general formula (2). If the amount of the surfactant used is less than the lower limit, the yield tends to decrease because of decrease in reaction rate. Meanwhile, if the amount of the surfactant used exceeds the upper limit, the purification step tends to be complicated.

Moreover, the amount of the heteropoly acid catalyst used is not particularly limited, and is preferably used at a ratio of 0.005 to 0.050 moles (more preferably 0.01 to 0.03 moles) per mole of the compound having the norbornene structure represented by the above-described general formula (2). If the amount of the heteropoly acid catalyst used is less than the lower limit, the yield tends to decrease because of decrease in reaction rate. Meanwhile, if the amount of the heteropoly acid catalyst used exceeds the upper limit, the reaction tends to proceed so rapidly that the reaction selectivity is deteriorated, resulting in decrease in yield.

In addition, the molar amount of the hydrogen peroxide solution used in terms of hydrogen peroxide is preferably in a range from 2.0 to 5.0 times and more preferably in a range from 2.2 to 3.0 times that of the carbon-carbon unsaturated bonds in the compound having the norbornene structure represented by the above-described general formula (2) as described above. If the molar amount of the hydrogen peroxide solution used is less than 2.0 times, the reaction does not proceed sufficiently. Meanwhile, if the molar amount of the hydrogen peroxide solution used exceeds 5.0 times, side reactions such as oxidative decomposition of the epoxy rings of the produced alicyclic diepoxy compound tend to proceed, resulting in decrease in yield.

Note that the temperature condition under which the compound having the norbornene structure represented by the above-described general formula (2), the surfactant, the hydrogen peroxide solution, and the heteropoly acid catalyst are introduced into the solvent, and the mixture is heated in the presence of the surfactant, the hydrogen peroxide solution, and the heteropoly acid catalyst is not particularly limited, and the temperature condition is preferably set, as appropriate, to be the above-described reaction temperature.

(Alicyclic Monoepoxy Compound of the Present Invention)

The alicyclic monoepoxy compound of the present invention is represented by the above-described general formula (3). $R^1$, $R^2$, and n in the general formula (3) have the same meanings as those of $R^1$, $R^2$, and n in the above-described general formula (1), and preferred ones thereof are also the same.

Note that, as described above, the alicyclic monoepoxy compound represented by the above-described general formula (3) can be obtained as a reaction intermediate (production intermediate) in producing the alicyclic diepoxy compound having the bis-spironorbornane structure represented by the above-described general formula (1) by using the compound having the norbornene structure represented by the above-described general formula (2) as a raw material compound.

(Monomer for Producing Polymer Material of the Present Invention)

A monomer for producing a polymer material of the present invention comprises the above-described alicyclic diepoxy compound of the present invention. Thus, the alicyclic diepoxy compound of the present invention can be used preferably as a monomer for producing a polymer material. For example, it is also possible to obtain an epoxy resin composition excellent in transparency and heat resistance by mixing the above-described alicyclic diepoxy compound of the present invention as a monomer for producing a polymer material (as a main agent or one of multiple monomer components serving as a main agent) with a curing agent, a curing accelerator, and the like, followed by curing.

(Applications of Alicyclic Diepoxy Compound of the Present Invention and Alicyclic Monoepoxy Compound of the Present Invention which is Intermediate Thereof, Etc.)

The alicyclic diepoxy compound of the present invention can be, for example, used as an epoxy compound or used in combination with another epoxy compound in an epoxy resin composition. The alicyclic diepoxy compound of the present invention is mixed, as appropriate, with a curing agent, an auxiliary catalyst, a curing accelerator, an optionally added filler, and the like to prepare a composition, and then the composition can be cured. Thus, an epoxy resin composition excellent in transparency and heat resistance can be obtained. The epoxy resin composition can be used as electronic materials and optical materials including a transparent resin (sealant) for covering light emitting elements such as light-emitting diodes. The alicyclic diepoxy compound according to the present invention can also be used as an intermediate (prepolymer) for special epoxy resins by being allowed to react with various bisphenols such as bisphenol A.

The alicyclic diepoxy compound of the present invention and the alicyclic monoepoxy compound of the present invention which is an intermediate thereof can be chemically modified by various epoxy ring-opening reactions, and are useful as reaction intermediates. For example, when the diepoxy compound is hydrolyzed in the presence of an acid catalyst, each epoxy group is converted to a diol having a trans structure.

Preferred Embodiment of Method for Producing Alicyclic Diepoxy Compound of the Present Invention Synthesis of Cyclohexanone-Based Bis-Spironorbornene A cyclohexanone-based bis-spironorbornene is, for example, synthesized according to Example 2 described in PTL 7 (paragraphs [0126] to [0132]) ("56%" in PTL 7). The "cyclohexanone-based bis-spironorbornene" referred herein is a compound represented by the general formula (2), in which n is 3, and each of $R^1$ and $R^2$ is a hydrogen atom. As described above, the cyclohexanone-based bis-spironorbornene can be synthesized according to Example 2 described in PTL 7 (paragraphs [0126] to [0132]).

Synthesis of Alicyclic Diepoxy Compound

An alicyclic diepoxide having a cyclohexanone-based bis-spironorbornane structure is synthesized by using the above-described cyclohexanone-based bis-spironorbornene as a raw material in the same manner as in the above-described method or a method employed in Example 1 described later (thus, an alicyclic diepoxide having a cyclohexanone-based bis-spironorbornane structure can also be synthesized). The obtained compound can be confirmed to have an alicyclic diepoxy compound structure represented by the following chemical formula (7) based on IR, $^1$H-NMR, $^{13}$C-NMR, and MS spectra:

[Chem. 8]

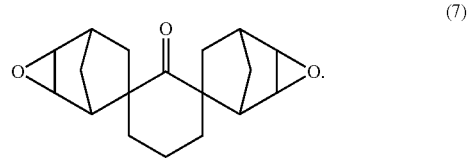

(7)

Other Preferred Embodiments of Method for Producing Alicyclic Diepoxy Compound of the Present Invention Synthesis of Other Alicyclic Diepoxy Compounds Also when n of the cycloalkanone ring in the general formula (1) is 4 (cycloheptanone) or 5 (cyclooctanone), the alicyclic diepoxides are synthesized in the same manner as in the above-described method or in a method employed in the example section described later through a compound having a cycloheptanone-based or cyclooctanone-based bis-spironorbornene structure (thus, other alicyclic diepoxides can also be synthesized).

EXAMPLES

Hereinafter, the present invention will be described more specifically on the basis of Examples and Comparative Examples; however, the present invention is not limited to Examples below.

Note that, in the following, the molecular structures of the compounds obtained in Examples were identified by measuring IR, NMR, and FD-MS spectra using IR measuring apparatuses (manufactured by JASCO Corporation under the trade names of FT/IR-460 and FT/IR-4100), NMR measuring apparatuses (manufactured by VARIAN under the trade name of UNITY INOVA-600 and manufactured by JEOL Ltd. under the trade name of JNM-Lambda 500), and an FD-MS measuring apparatus (manufactured by JEOL Ltd. under the trade name of JMS-700V).

Synthesis of Raw Material "Cyclopentanone-Based Bis-Spironorbornene"

<First Step>

First, to a 1 L three-necked flask, 30.86 g (378.5 mmol) of dimethylamine hydrochloride was added. Next, to the three-necked flask, 12.3 g (385 mmol) of 26 paraformaldehyde, 23.9 g (385 mmol) of ethylene glycol, and 12.95 g (154 mmol) of cyclopentanone were further added. Subsequently, to the three-necked flask, 16.2 g (165 mmol) of methylcyclohexane was added, and then 0.4 g of 35% by mass hydrochloric acid (HCl: 3.85 mmol) was added to obtain a first mixture liquid. Note that the acid (HCl) content in the first mixture liquid was 0.025 mole equivalents to the ketone group in the cyclopentanone (3.85 [molar amount of HCl]/154 [molar amount of cyclopentanone]=0.025).

Subsequently, the inside of the three-necked flask was purged with nitrogen, and the first mixture liquid was stirred under heating for 8 hours at a temperature inside the three-necked flask of 85° C. at normal pressure (0.1 MPa). Thus, a reaction liquid containing a Mannich base represented by the following chemical formula (4) was obtained:

[Chem. 9]

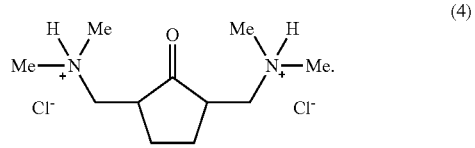

(4)

<Second Step>

Next, the reaction liquid in the three-necked flask was cooled to 50° C., and then methanol (250 ml), 4.17 g of a 50% by mass aqueous dimethylamine solution (dimethylamine: 46.2 mmol), and 30.5 g (461.5 mmol) of cyclopentadiene were added to the reaction liquid in the three-necked flask to obtain a second mixture liquid. Subsequently, the inside of the three-necked flask was purged with nitrogen, and after the temperature inside the three-necked flask was raised to 65° C. at normal pressure (0.1 MPa), the second mixture liquid was stirred under heating at 65° C. for 5 hours. Thus, the compound was formed.

Subsequently, the second mixture liquid in the three-necked flask was concentrated by azeotropy of methylcyclohexane with methanol to remove 100 mL of liquid from the second mixture liquid. Note that by removing 100 mL of the liquid, most methylcyclohexane (75% by mass of the whole amount of methylcyclohexane in the second mixture liquid before the concentration) was removed from the second mixture liquid. Next, the second mixture liquid from which methylcyclohexane had been removed was cooled under a temperature condition of −20° C. for 12 hours to precipitate crystals, and then the crystals were collected by vacuum filtration. The thus obtained crystals were subjected to a washing step with 20 mL of methanol at −20° C. three times, and then methanol was removed by evaporation. Thus, 17.4 g (yield: 47%) of a product was obtained.

IR and NMR ($^1$H-NMR and $^{13}$C-NMR) measurements were conducted to determine the structure of the thus obtained compound, and the compound was found to be 5-norbornene-2-spiro-2'-cyclopentanone-5'-spiro-2"-5"-norbornene represented by the following chemical formula (5):

[Chem. 10]

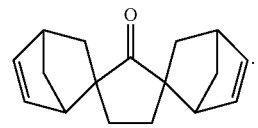

(5)

Example 1

(Synthesis of Alicyclic Diepoxy Compound)

To a 1 L two-necked flask equipped with a reflux tube, cetylpyridinium chloride (467 mg, 1.37 mmol), 5-norbornene-2-spiro-2'-cyclopentanone-5'-spiro-2"-5"-norbornene (10.0 g, 41.6 mmol), and 400 mL of chloroform were added, followed by stirring at room temperature. Meanwhile, to a 200 mL recovery flask equipped with a reflux tube, $H_3PW_{12}O_{40}$ (1.32 g, 0.458 mmol) and a hydrogen peroxide solution (concentration: 30% by weight, 21.1 g, 186 mmol) were added and stirred for 30 minutes under heating at 60° C. By cooling the mixture to room temperature, a yellow solution was obtained. This solution was added to the above-described 1 L two-necked recovery flask, and stirred under heating at 40° C. To check the progress of the reaction, an aliquot of the reaction solution was taken out and measured by $^1$H-NMR during the reaction. The result showed the formation of the monoepoxide intermediate and the diepoxide product, and hence the reaction was continued. After 4.5 hours had passed from the start of the heating, the reaction was found to be completed, and the stirring was stopped, followed by cooling to room temperature. The solution was transferred to a separatory funnel and subjected to a liquid-liquid extraction operation, and the aqueous layer was removed. Next, 50 mL of an aqueous sodium thiosulfate solution at a concentration of 10% by weight was prepared. This solution was added to the organic layer, followed by a liquid-liquid extraction operation, and the aqueous layer was removed. Next, 50 mL of an aqueous sodium carbonate solution at a concentration of 5% by weight was prepared. This solution was added to the organic layer, followed by a liquid-liquid extraction operation, and the aqueous layer was discarded. Next, 100 mL of pure water was added to the organic layer, followed by a liquid-liquid extraction operation, and the aqueous layer was discarded. The organic layer was transferred to a 1 L Erlenmeyer flask, and dried by adding anhydrous sodium sulfate. After filtration, the filtrate was concentrated to obtain a light yellow powdery crude product. This crude product was purified by a recrystallization operation (the solvent used was methanol) to obtain 7.38 g of a white product (yield: 65.1%).

Figure 2:
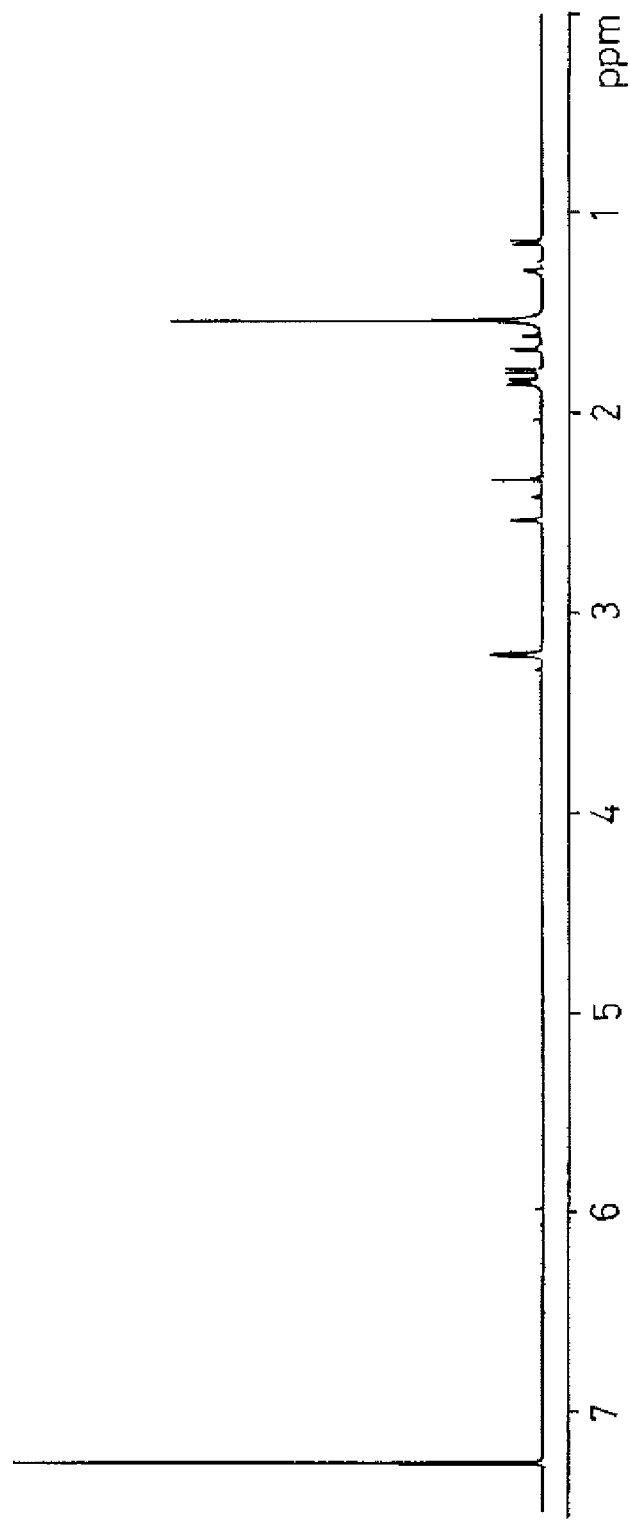
FIG. 2 is a chart showing a $^1$H-NMR (solvent: $CDCl_3$) spectrum of the alicyclic diepoxy compound represented by chemical formula (6) and obtained in Example 1.
Figure 3:
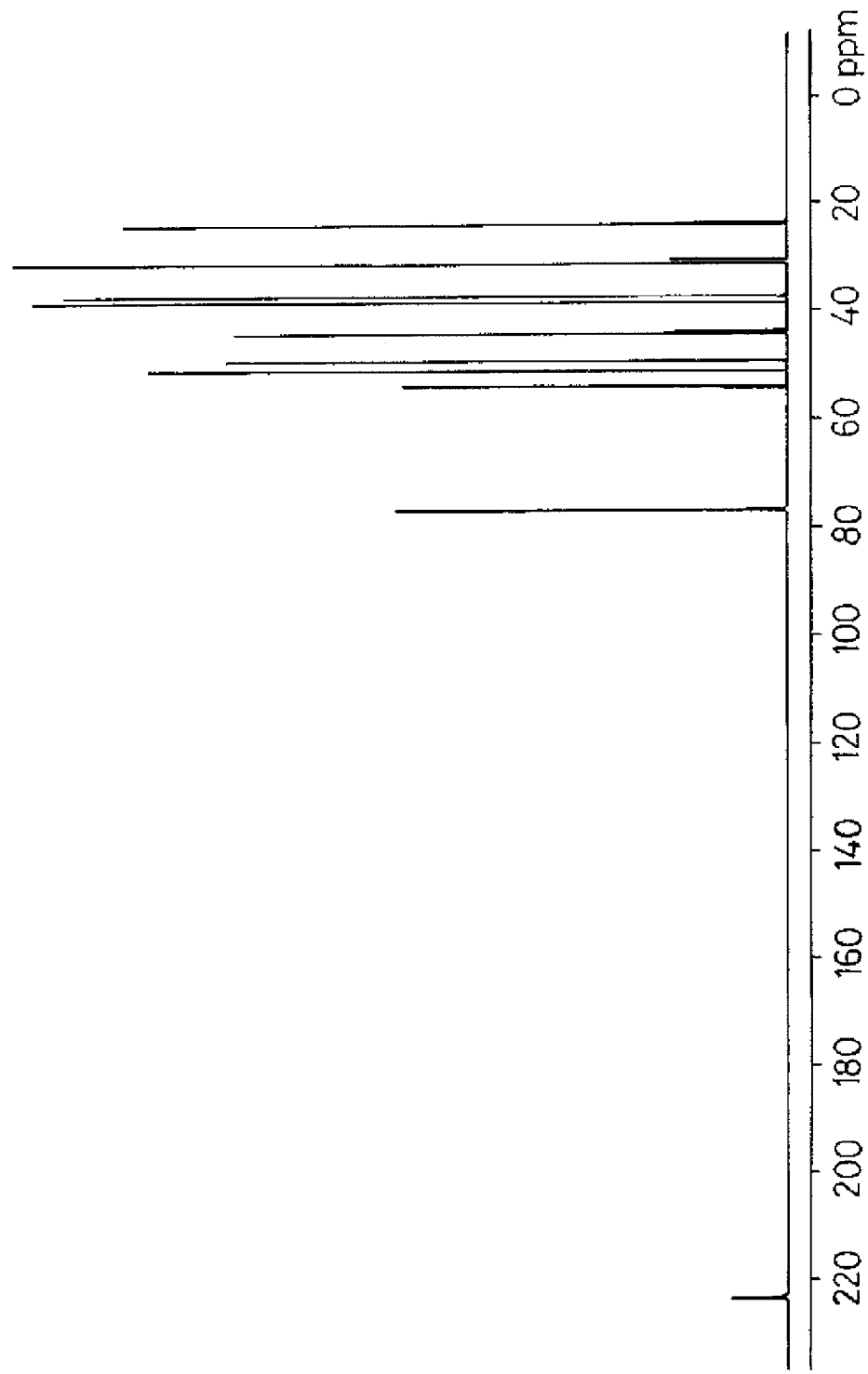
FIG. 3 is a chart showing a $^{13}$C-NMR (solvent: $CDCl_3$) spectrum of the alicyclic diepoxy compound represented by chemical formula (6) and obtained in Example 1.
Figure 4:
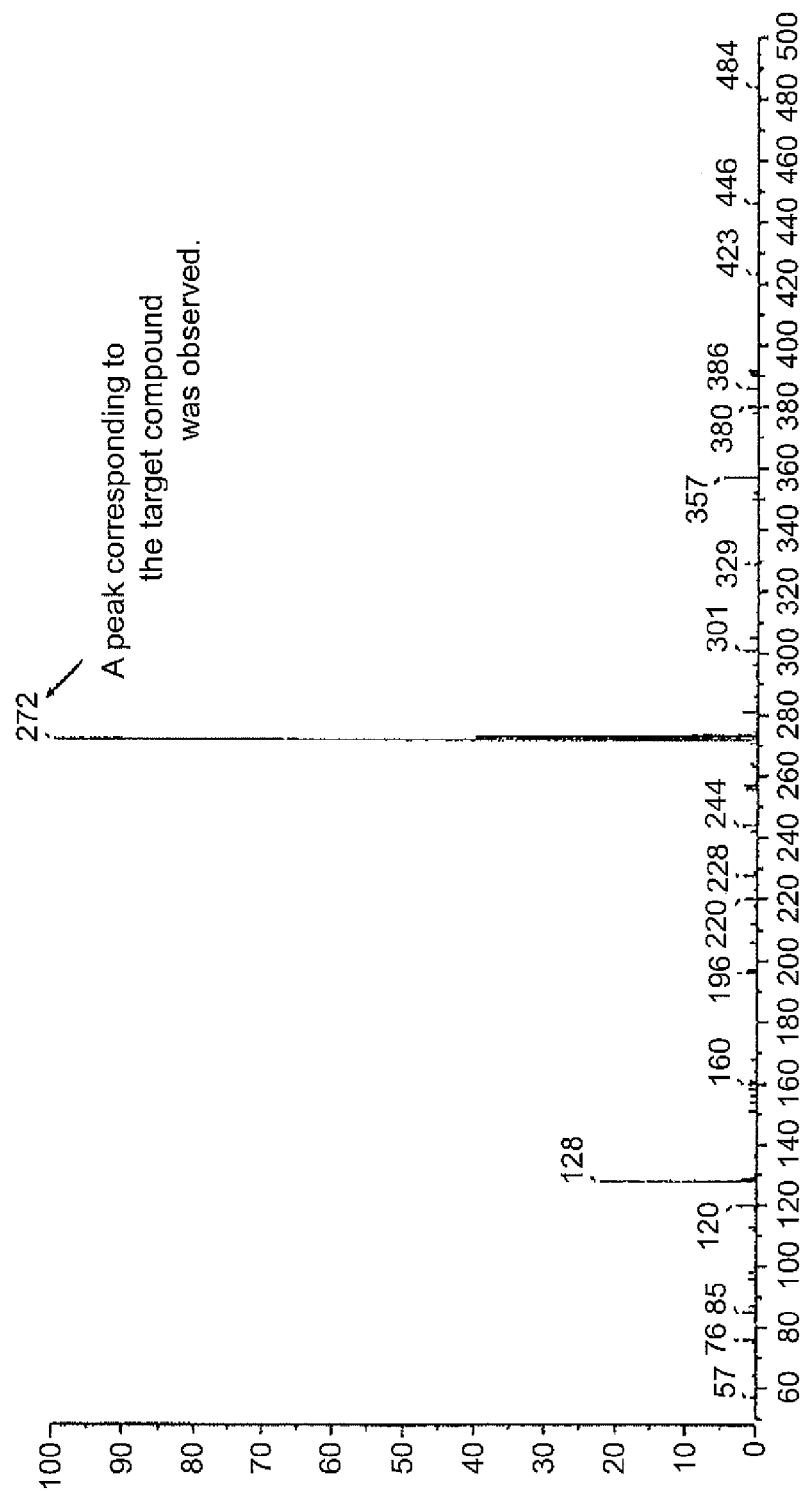
FIG. 4 is a chart showing an FD-MS spectrum of the alicyclic diepoxy compound represented by chemical formula (6) and obtained in Example 1.

IR, NMR ($^1$H-NMR and $^{13}$C-NMR), and MS measurements were conducted to determine the structure of the thus obtained compound. FIG. 1 shows an IR spectrum of the thus obtained compound, FIG. 2 shows a $^1$H-NMR (CDCl$_3$) spectrum thereof, FIG. 3 shows a $^{13}$C-NMR (CDCl$_3$) spectrum thereof, and FIG. 4 shows an MS spectrum thereof. From the results shown in FIGS. 1 to 4, the obtained compound was identified to be an alicyclic diepoxy compound represented by the following chemical formula (6):

[Chem. 11]

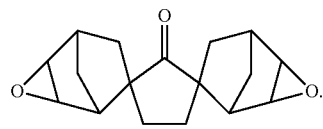

(6)

Note that, in the MS spectrum shown in FIG. 4, a peak corresponding to the alicyclic diepoxy compound represented by the above-described chemical formula (6) was observed at a position of 272 (m/z).

INDUSTRIAL APPLICABILITY

The alicyclic diepoxy compounds having the bis-spironorbornane structure according to the present invention are synthesized from the corresponding alicyclic compounds having the bis-spironorbornene structure by epoxidation in a usual manner in relatively high yields, and are useful as monomers for producing polymer materials having high transparency and high heat resistance. In addition, these compounds have higher solubilities in organic solvents and hence are easier to handle in the manufacturing process of the polymer materials, compared to other multifunctional compounds used for heat-resistant polymer materials. In addition, these compounds are also applicable as reaction intermediates of various useful compounds such as pharmaceuticals and agricultural chemicals.

The invention claimed is:

1. An alicyclic diepoxy compound represented by the following general formula (1):

[Chem. 1]

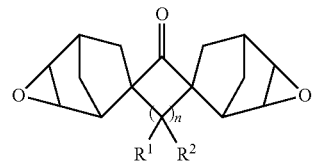

(1)

(in the general formula (1), R$^1$ and R$^2$ each independently represent one selected from the group consisting of a hydrogen atom, alkyl groups having 1 to 10 carbon atoms, and a fluorine atom, and n represents an integer of 2 to 5).

2. The alicyclic diepoxy compound according to claim 1, wherein
n in the general formula (1) is 2 or 3.

3. The alicyclic diepoxy compound according to claim 1, wherein
n in the general formula (1) is 2.

4. A method for producing an alicyclic diepoxy compound having a bis-spironorbornane structure represented by the following general formula (1), the method comprising:
epoxidizing one carbon-carbon unsaturated bond in a compound having a norbornene structure represented by the following general formula (2) to obtain an alicyclic monoepoxy compound represented by the following general formula (3); and
epoxidizing another carbon-carbon unsaturated bond in the obtained compound to obtain the alicyclic diepoxy compound represented by the following general formula (1):

[Chem. 2]

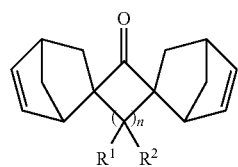

(2)

(in the general formula (2), R$^1$ and R$^2$ each independently represent one selected from the group consisting of a hydrogen atom, alkyl groups having 1 to 10 carbon atoms, and a fluorine atom, and n represents an integer of 2 to 5);

[Chem. 3]

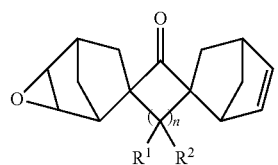

(3)

(in the general formula (3), R$^1$ and R$^2$ each independently represent one selected from the group consisting of a hydrogen atom, alkyl groups having 1 to 10 carbon atoms, and a fluorine atom, and n represents an integer of 2 to 5); and

[Chem. 4]

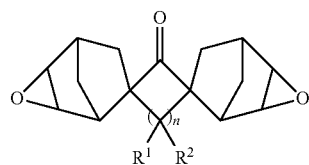

(1)

(in the general formula (1), R$^1$ and R$^2$ each independently represent one selected from the group consisting of a hydrogen atom, alkyl groups having 1 to 10 carbon atoms, and a fluorine atom, and n represents an integer of 2 to 5).

5. The method for producing an alicyclic diepoxy compound according to claim 4, wherein
n in the general formula (1) is 2 or 3.

6. The method for producing an alicyclic diepoxy compound according to claim 4, wherein
n in the general formula (1) is 2.

7. The method for producing an alicyclic diepoxy compound according to claim 4, wherein
an epoxidation reaction is conducted in the presence of a hydrogen peroxide solution, a heteropoly acid catalyst, and a surfactant.

8. An alicyclic monoepoxy compound represented by the following general formula (3):

[Chem. 5]

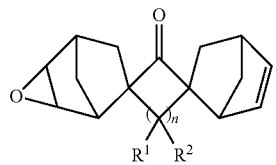

(3)

(in the general formula (3), $R^1$ and $R^2$ each independently represent one selected from the group consisting of a hydrogen atom, alkyl groups having 1 to 10 carbon atoms, and a fluorine atom, and n represents an integer of 2 to 5).

9. The alicyclic monoepoxy compound according to claim 8, wherein n in the general formula (3) is 2 or 3.

10. The alicyclic monoepoxy compound according to claim 8, wherein n in the general formula (3) is 2.

* * * * *